United States Patent
Corrigan, Jr.

(10) Patent No.: US 10,470,778 B2
(45) Date of Patent: Nov. 12, 2019

(54) RADIAL COMPRESSION HEMOSTASIS BAND WITH DOPPLER CONFIRMING VASCULAR PATENCY

(71) Applicant: Richard F. Corrigan, Jr., Wheaton, IL (US)

(72) Inventor: Richard F. Corrigan, Jr., Wheaton, IL (US)

(*) Notice: Subject to any disclaimer, the term of this patent is extended or adjusted under 35 U.S.C. 154(b) by 579 days.

(21) Appl. No.: 15/177,221

(22) Filed: Jun. 8, 2016

(65) Prior Publication Data

US 2016/0354090 A1 Dec. 8, 2016

Related U.S. Application Data

(60) Provisional application No. 62/172,658, filed on Jun. 8, 2015.

(51) Int. Cl.
| | |
|---|---|
| *A61B 17/132* | (2006.01) |
| *A61B 8/00* | (2006.01) |
| *A61B 17/135* | (2006.01) |
| *A61B 8/06* | (2006.01) |
| *A61B 8/08* | (2006.01) |
| *A61B 17/00* | (2006.01) |

(52) U.S. Cl.
CPC ............ *A61B 17/1325* (2013.01); *A61B 8/06* (2013.01); *A61B 8/4227* (2013.01); *A61B 8/488* (2013.01); *A61B 17/135* (2013.01); *A61B 8/4455* (2013.01); *A61B 2017/00902* (2013.01)

(58) Field of Classification Search
CPC ....... A61B 17/132; A61B 17/135; A61B 8/00; A61B 8/06; A61B 8/08

USPC .................................................. 606/201, 203
See application file for complete search history.

(56) References Cited

U.S. PATENT DOCUMENTS

| | | |
|---|---|---|
| 3,620,209 A | 11/1971 | Kravitz |
| 4,479,494 A | 10/1984 | McEwen |
| 4,509,528 A | 4/1985 | Harvinder et al. |
| 4,548,198 A | 10/1985 | Manes |
| 4,834,802 A | 5/1989 | Prier |
| 5,269,803 A | 12/1993 | Geary et al. |
| 5,307,811 A | 5/1994 | Sigwart et al. |
| 5,584,853 A | 12/1996 | McEwen et al. |
| 5,643,315 A | 7/1997 | Daneshvar |

(Continued)

FOREIGN PATENT DOCUMENTS

| | | |
|---|---|---|
| EP | 2404549 | 8/2011 |
| EP | 2708215 | 8/2012 |

(Continued)

OTHER PUBLICATIONS

International Search Report and Written Opinion from PCT Application No. PCT/US2016/036501 entitled: Radial Compression Hemostasis Band With Doppler Confirming Vascular Patency (Search Report and Written Opinion dated Aug. 30, 2016).

(Continued)

*Primary Examiner* — Vy Q Bui
(74) *Attorney, Agent, or Firm* — Hovey Williams LLP (57) ABSTRACT

A radial compression band is configured to provide hemostatic compression to an arterial access site on the arm of a wearer. The radial compression band includes an elongated arm band that presents an arm opening sized to receive the arm. The arm band presents proximal and distal margins, with the arm opening being defined between the margins.

27 Claims, 9 Drawing Sheets

(56) References Cited

U.S. PATENT DOCUMENTS

| | | |
|---|---|---|
| 5,709,647 A | 1/1998 | Ferber |
| 5,842,996 A | 12/1998 | Gruenfeld et al. |
| 6,361,496 B1 | 3/2002 | Zikorus et al. |
| 6,565,592 B2 | 5/2003 | Mach |
| 7,331,977 B2 | 2/2008 | McEwen et al. |
| 7,479,154 B2 | 1/2009 | McEwen et al. |
| 7,485,131 B2 | 2/2009 | Hovanes et al. |
| 7,510,530 B2 | 3/2009 | Hashimoto et al. |
| 8,048,105 B2 | 11/2011 | McEwen et al. |
| 8,114,026 B2 | 2/2012 | Leschinsky |
| 8,137,276 B2 | 3/2012 | Petruzzello et al. |
| 8,231,558 B2 | 7/2012 | Singh |
| 8,353,834 B2 | 1/2013 | Routh et al. |
| 8,366,740 B2 | 2/2013 | McEwen et al. |
| 8,425,426 B2 | 4/2013 | McEwen et al. |
| 8,721,678 B2 | 5/2014 | McEwen et al. |
| 8,764,789 B2 | 7/2014 | Ganske et al. |
| 2006/0076376 A1 | 4/2006 | Kemery et al. |
| 2006/0122513 A1 | 6/2006 | Taylor |
| 2007/0066897 A1 | 3/2007 | Sekins et al. |
| 2009/0281565 A1 | 11/2009 | McNeese |
| 2010/0010404 A1 | 1/2010 | Nardi et al. |
| 2010/0179586 A1 | 7/2010 | Ward et al. |
| 2011/0028934 A1 | 2/2011 | Buckman et al. |
| 2011/0224592 A1 | 9/2011 | Buckman et al. |
| 2012/0053617 A1 | 3/2012 | Benz et al. |
| 2012/0232579 A1 | 9/2012 | Lee |
| 2013/0085524 A1 | 4/2013 | Dahlberg et al. |
| 2013/0190806 A1 | 7/2013 | McEwen et al. |
| 2013/0237866 A1 | 9/2013 | Cohen et al. |
| 2014/0012120 A1 | 1/2014 | Cohen et al. |
| 2014/0024986 A1 | 1/2014 | Souma |
| 2014/0073973 A1 | 3/2014 | Sexton et al. |
| 2014/0142615 A1* | 5/2014 | Corrigan, Jr. ...... A61B 17/1325 606/201 |
| 2014/0336697 A1 | 11/2014 | Masaki |
| 2014/0343600 A1 | 11/2014 | Leschinsky |
| 2015/0018869 A1 | 1/2015 | Benz et al. |
| 2015/0119773 A1 | 4/2015 | Flannery et al. |

FOREIGN PATENT DOCUMENTS

| | | |
|---|---|---|
| EP | 1382306 | 1/2014 |
| JP | 3136041 | 10/2007 |
| WO | WO9846144 | 10/1998 |
| WO | WO2009012473 | 1/2009 |
| WO | WO2014027347 | 2/2014 |
| WO | WO2014075627 | 5/2014 |
| WO | WO2014125637 | 8/2014 |

OTHER PUBLICATIONS

Office Action from U.S. Appl. No. 14/086,778 (dated Jan. 21, 2016).
Office Action from U.S. Appl. No. 14/086,778 (dated Jun. 30, 2015).
International Search Report and Written Opinion from PCT Serial No. PCT/US2013/071320 (dated Feb. 27, 2014).
Terumo Medical Corporation, TR Band: Radial Compression Device; p. 10 (Copyright dated 2007) at http://www.terumois.com/admisitration/pdfs/collateral%20library/TR%20Band%20Sell%20sheet.pdf.
Advanced Vascular Dynamics; A leader in post-catheterization hemostasis; (Copyright dated 2013) at www.comporessar.com/products/radial-hemostasis.php.
Vascular Solutions, Inc.; 2013 Product Catalog; (Copyright dated 2013) at http://vasc.com/wp-contest/uploads/2011/12/VSI-Product-Catalog-ML-1591-Rev-N.pdf.
NPL from Dec. 31, 2014 letter: Duncan Graham-Rowe, An Ultrasonic Tourniquet to Stop Battlefield Bleeding, MIT Technology at http://www.technology.com/news406163/anultrasonic-tourniquet-to-stop-battlefield-bleeding/.
European Search Report from EP Application No. 16808214.7 entitled Radial Compression Hemostasis Band With Doppler Confirming Vascular Patency (Search Report dated Jan. 25, 2019).

* cited by examiner

RADIAL COMPRESSION HEMOSTASIS BAND WITH DOPPLER CONFIRMING VASCULAR PATENCY

RELATED APPLICATION

This application claims the benefit of U.S. Provisional Application Ser. No. 62/172,658, filed Jun. 8, 2015, entitled RADIAL COMPRESSION HEMOSTASIS BAND WITH DOPPLER CONFIRMING VASCULAR PATENCY, which is hereby incorporated in its entirety by reference herein.

BACKGROUND

1. Field

The present invention relates generally to hemostasis devices. More specifically, embodiments of the present invention concern a radial compression band to gain hemostasis of an arterial access site while maintaining patency of the accessed artery.

2. Discussion of Prior Art

Vascular intervention procedures have long been performed by accessing the femoral artery. However, access of the radial artery has become accepted as an alternative to femoral artery intervention. For instance, it has been found that intervention of the radial artery reduces costs and potential complications when compared to femoral artery invention. Following the intervention, hemostasis of the access site is achieved by applying a hemostasis compression band to the site or by applying manual pressure to the site.

However, certain deficiencies exist with respect to conventional devices for gaining hemostasis of an arterial access site, including those used to provide hemostasis of a radial access site. For instance, conventional hemostasis devices (including compression bands), while being able to provide the necessary pressure to achieve hemostasis, are known to collapse the radial artery when applying pressure. It is also known that the radial artery can be occluded if the artery is either partly or completely collapsed. Occlusion of the radial artery can restrict adequate blood supply to the hand, causing complications such as pain and numbness in the hand.

To further complicate the task of maintaining radial artery patency, it is known that limited blood flow through the radial artery can occur even when the radial artery is occluded. For instance, retrograde blood flow in the radial artery (i.e., blood flow in a direction from the fingers toward the elbow) can occur when the radial artery is occluded. Conventional systems can mistakenly identify patency of the artery during this occluded condition.

SUMMARY

The following brief summary is provided to indicate the nature of the subject matter disclosed herein. While certain aspects of the present invention are described below, the summary is not intended to limit the scope of the present invention.

Embodiments of the present invention provide a radial compression band that does not suffer from the problems and limitations of the prior art hemostat devices set forth above.

A first aspect of the present invention concerns a radial compression band configured to provide hemostatic compression to an arterial access site on the arm of a wearer. The radial compression band broadly includes an elongated arm band, and an expandable bladder. The arm band presents an arm opening sized to receive the arm. The arm band presents proximal and distal margins, with the arm opening being defined between the margins. The arm band presents a window located at least in part between the proximal and distal margins so as to expose the underlying portion of the arm. The expandable bladder is operable to apply adjustable hemostatic pressure to the access site. The bladder is positioned at least in part radially inward of the window and extends across at least part of the window. The bladder is at least substantially transparent so as to facilitate viewing of the access site.

A second aspect of the present invention concerns a radial compression band configured to provide hemostatic compression to an arterial access site on the arm of a wearer after an arterial sheath is removed from the access site. The radial compression band broadly includes an elongated arm band, an arterial pressure surface, and a Doppler probe. The arm band presents an arm opening sized to receive the arm. The arm band presents proximal and distal margins, with the arm opening being defined between the margins. The arterial pressure surface faces radially inward relative to the arm band for compressive engagement with the access site. The Doppler probe is coupled to the arm band and is spaced from the pressure surface to sense blood flow past the access site and through the artery and thereby facilitate arterial patency during hemostasis of the site. The arm band presents an access opening located between the pressure surface and the Doppler probe, with the access opening being configured to receive the arterial sheath when the radial compression band is donned.

A third aspect of the present invention concerns a radial compression band configured to provide hemostatic compression to an arterial access site on the arm of a wearer. The radial compression band broadly includes an elongated arm band that extends circumferentially to present an arm opening sized to receive the arm. The arm band presents proximal and distal margins, with the arm opening being defined between the margins. The arm band is partly sectioned to include circumferentially extending, proximal and distal arm band sections. The arm band presents a circumferential slot defined between the sections along at least half of the circumferential length of the arm band, such that the arm band sections are joined along a circumferential minority of the arm band.

A fourth aspect of the present invention concerns a radial compression band configured to provide hemostatic compression to an arterial access site on the arm of a wearer after an arterial sheath is removed from the access site. The radial compression band broadly includes an elongated arm band, an arterial pressure surface, and a Doppler probe. The arm band presents an arm opening sized to receive the arm. The arm band presents proximal and distal margins, with the arm opening being defined between the margins. The arterial pressure surface faces radially inward relative to the arm band for compressive engagement with the access site. The Doppler probe is coupled to the arm band and is spaced from the pressure surface to sense blood flow through the artery and thereby facilitate arterial patency during hemostasis of the site. The arm band presents an access opening located between the pressure surface and the Doppler probe, with the access opening being configured to receive the arterial sheath when the radial compression band is donned. The pressure surface, Doppler probe, and access opening are aligned circumferentially along the arm band.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Preferred embodiments of the invention are described in detail below with reference to the attached drawing figures, wherein.

The drawing figures do not limit the present invention to the specific embodiments disclosed and described herein. The drawings are not necessarily to scale, emphasis instead being placed upon clearly illustrating the principles of the preferred embodiment.

DETAILED DESCRIPTION OF THE PREFERRED EMBODIMENTS

Figure 1:
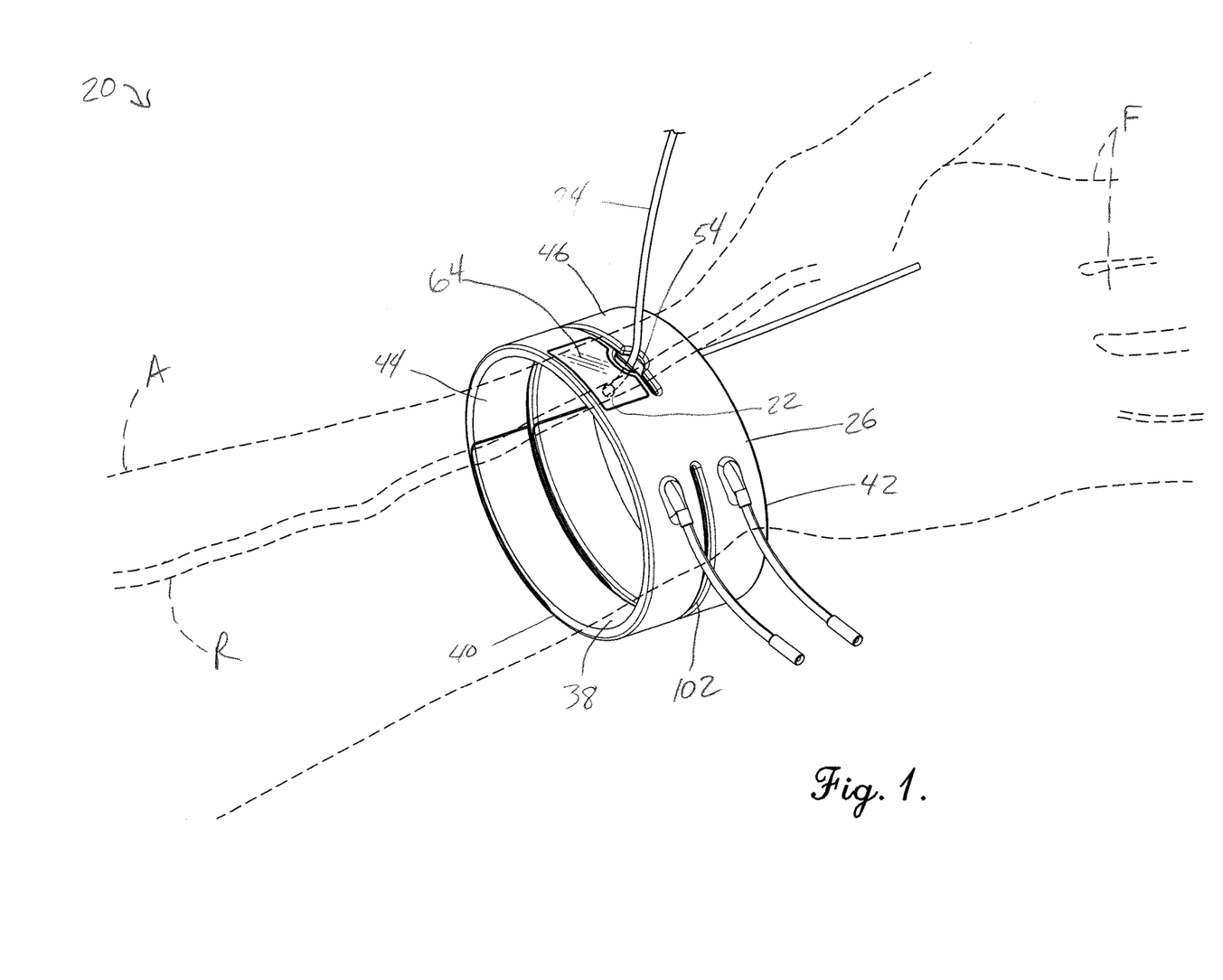
FIG. 1 is an upper perspective of a radial compression band constructed in accordance with a preferred embodiment of the present invention, showing the radial compression band positioned over a radial access site on a patient's forearm.
Figure 2:
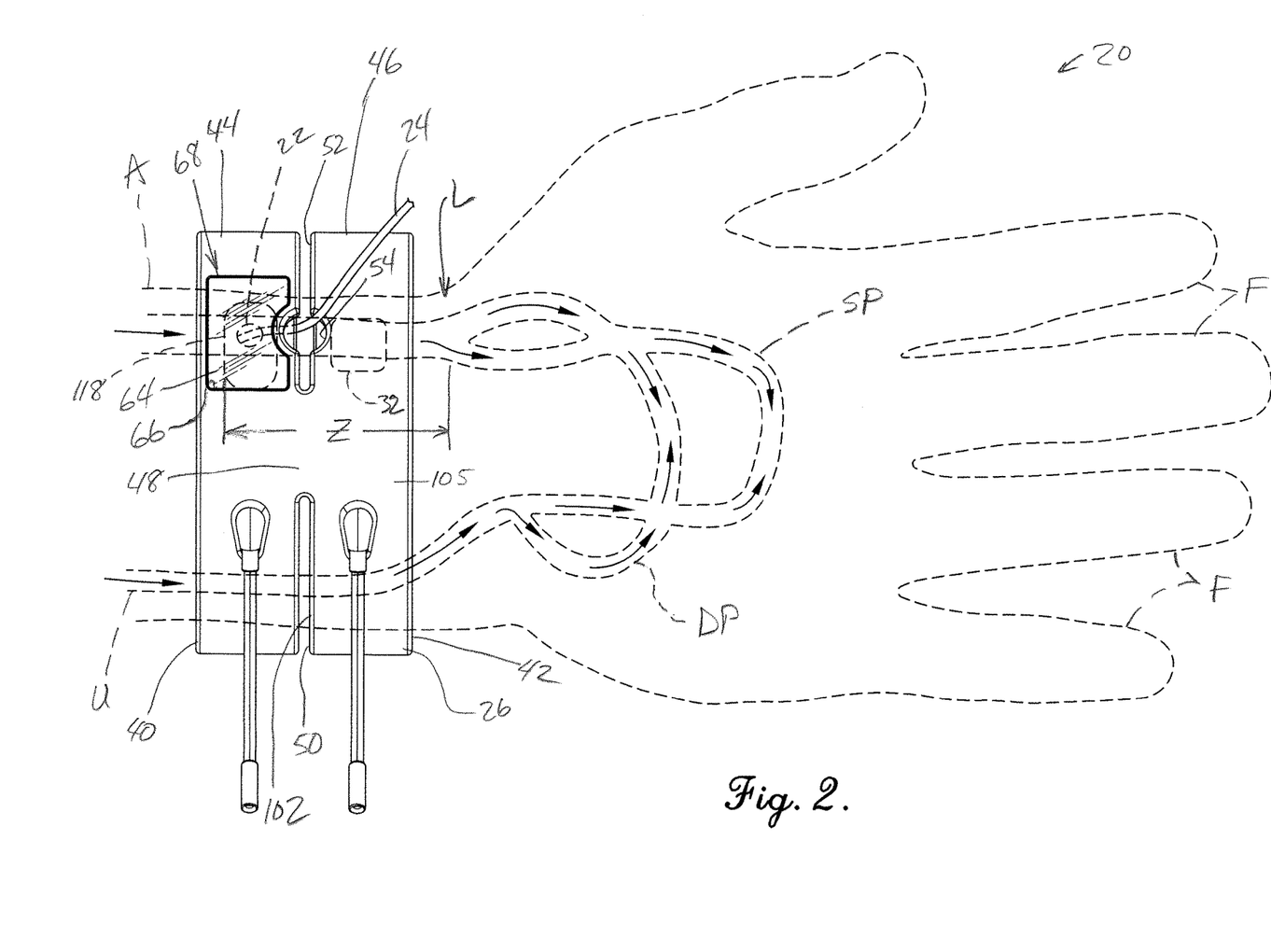
FIG. 2 is a top view of the radial compression band shown in FIG. 1, showing the compression band donned by the patient, with the arm band including a window to facilitate viewing of the access site, and with the patient's forearm being shown schematically to illustrate antegrade blood flow through radial and ulnar arteries and through the palmar arches.
Figure 3:
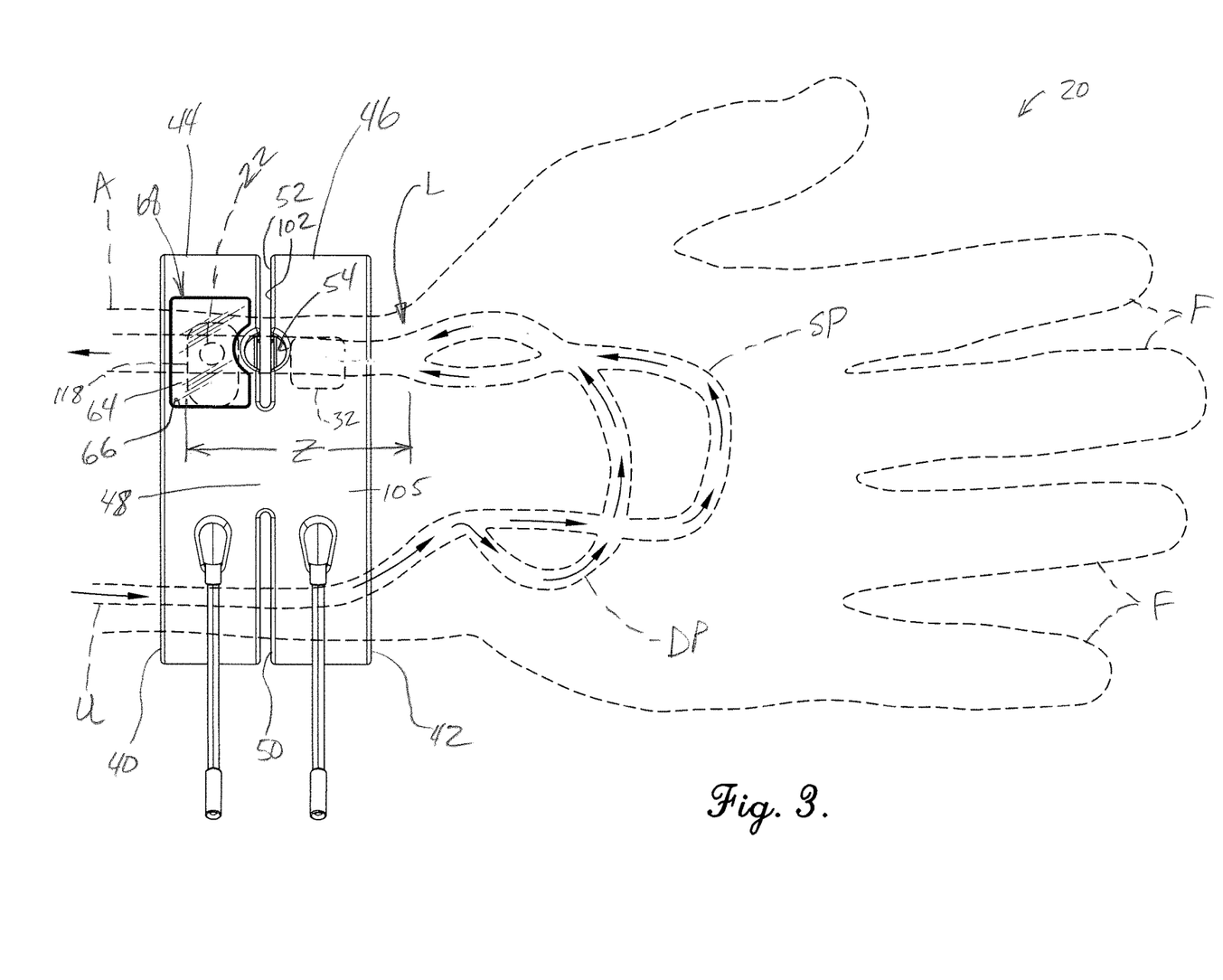
FIG. 3 is a top view of the radial compression band similar to FIG. 2, but showing retrograde blood flow through the radial artery and the palmar arches.
Figure 4:
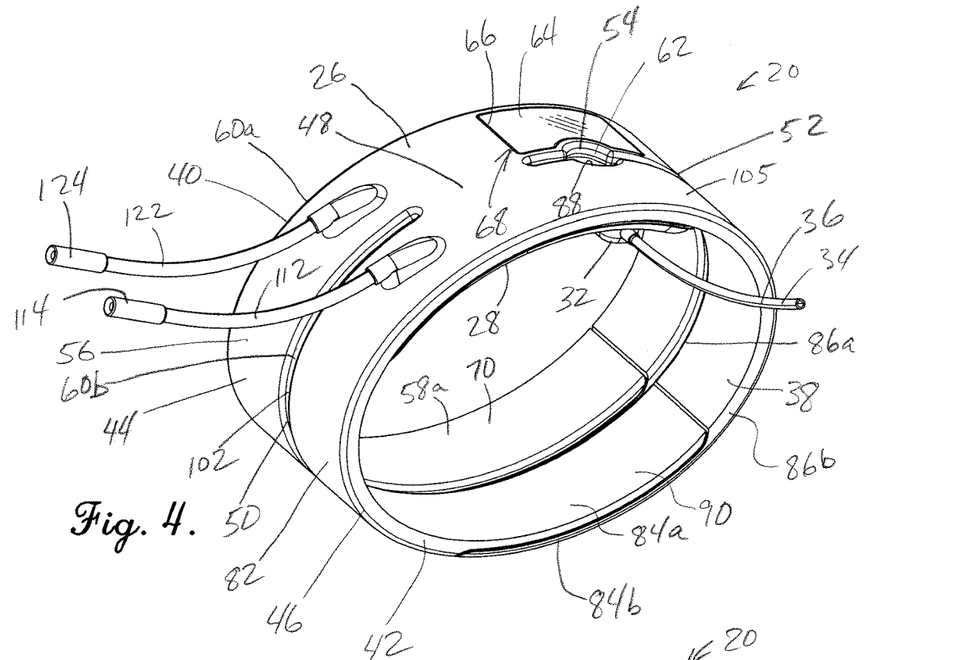
FIG. 4 is an upper perspective of the radial compression band shown in FIGS. 1-3, particularly showing the Doppler probe supported on a probe bladder of the radial compression band, with the radial compression band being in a coiled configuration.

Turning initially to FIGS. 1-3, a radial compression band 20 is part of a system that is configured to provide hemostatic compression to an arterial access site 22 on the arm A of a wearer. In the illustrated embodiment, the band 20 preferably provides compression to the access site 22 associated with a radial artery R. The band 20 is preferably used to establish patent hemostasis of the access site 22 so as to maintain blood flow through the radial artery R.

The arm A includes a distally extending radial artery R and a distally extending ulnar artery U (see FIGS. 2 and 3). A deep palmar arch DP is formed by the radial artery R. A superficial palmar arch SP is formed by the ulnar artery U. During normal antegrade flow, blood generally flows distally from the elbow (not shown) toward fingers F (see FIG. 2).

Retrograde flow (see FIG. 3) can occur when the radial artery R is occluded at the access site 22. During retrograde flow, blood flows from the ulnar artery U through the deep palmar arch DP and/or the superficial palmar arch SP. Retrograde flow generally occurs if there is no antegrade flow past the access site 22 or if antegrade flow past the access site 22 is reduced to a point that pressure from one or both of the palmar arches SP,DP is greater than the pressure from the radial artery R at the access site 22.

A catheter sheath 24 penetrates the illustrated access site 22 to access the radial artery R. While the catheter sheath 24 is illustrated as being inserted into the access site 22 while the band 20 is located on the arm A, the sheath 24 can be (and is typically) removed from the access site 22 either before or after the band 20 is positioned on the arm A. Additionally, although the illustrated band 20 is preferably used in connection with accessing the radial artery R, it is within the ambit of the present invention where the band 20 is used with another artery.

As will be discussed, the band 20 is preferably configured to achieve hemostasis of the access site 22 while sensing blood flow through a zone Z of the radial artery R. The zone Z extends between a location just proximal of the access site 22 and an anastomosis location L where the superficial palmar arch SP meets the radial artery R (see FIGS. 2 and 3). The band 26 can preferably sense blood flow through the zone Z and sense whether the blood flow is antegrade flow or retrograde flow.

The radial compression band 20 broadly includes an elongated arm band 26, a probe bladder 28, a hemostasis bladder 30, and a Doppler probe 32.

Figure 5:
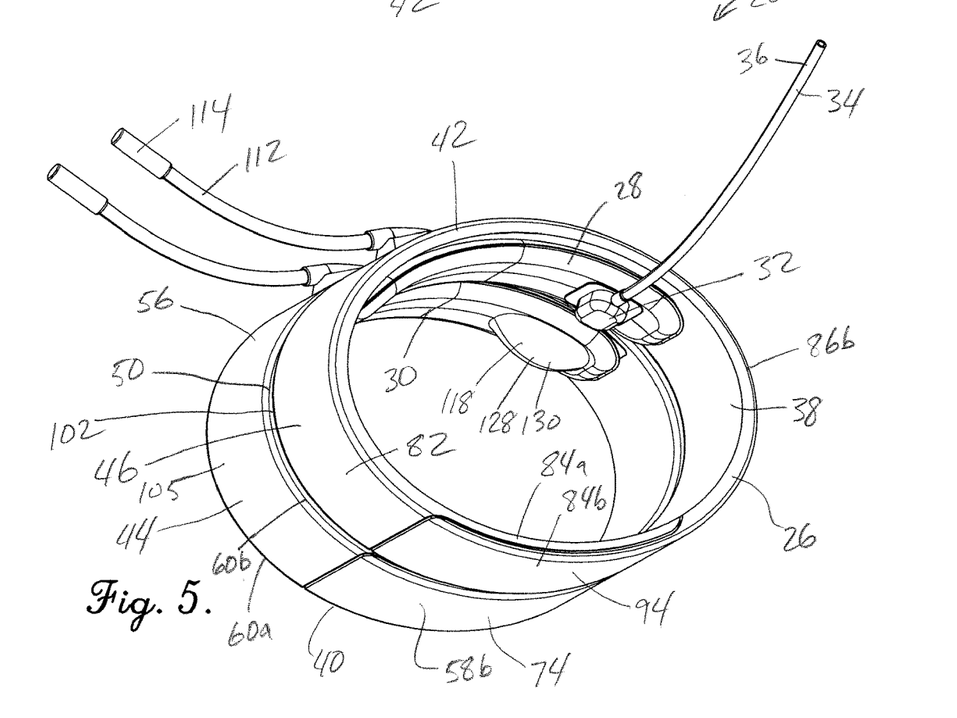
FIG. 5 is a lower perspective of the radial compression band shown in FIGS. 1-4, showing a hemostasis bladder spaced axially from the probe bladder, with the hemostasis bladder including a hemostasis pad located proximally from the Doppler probe.
Figure 7:
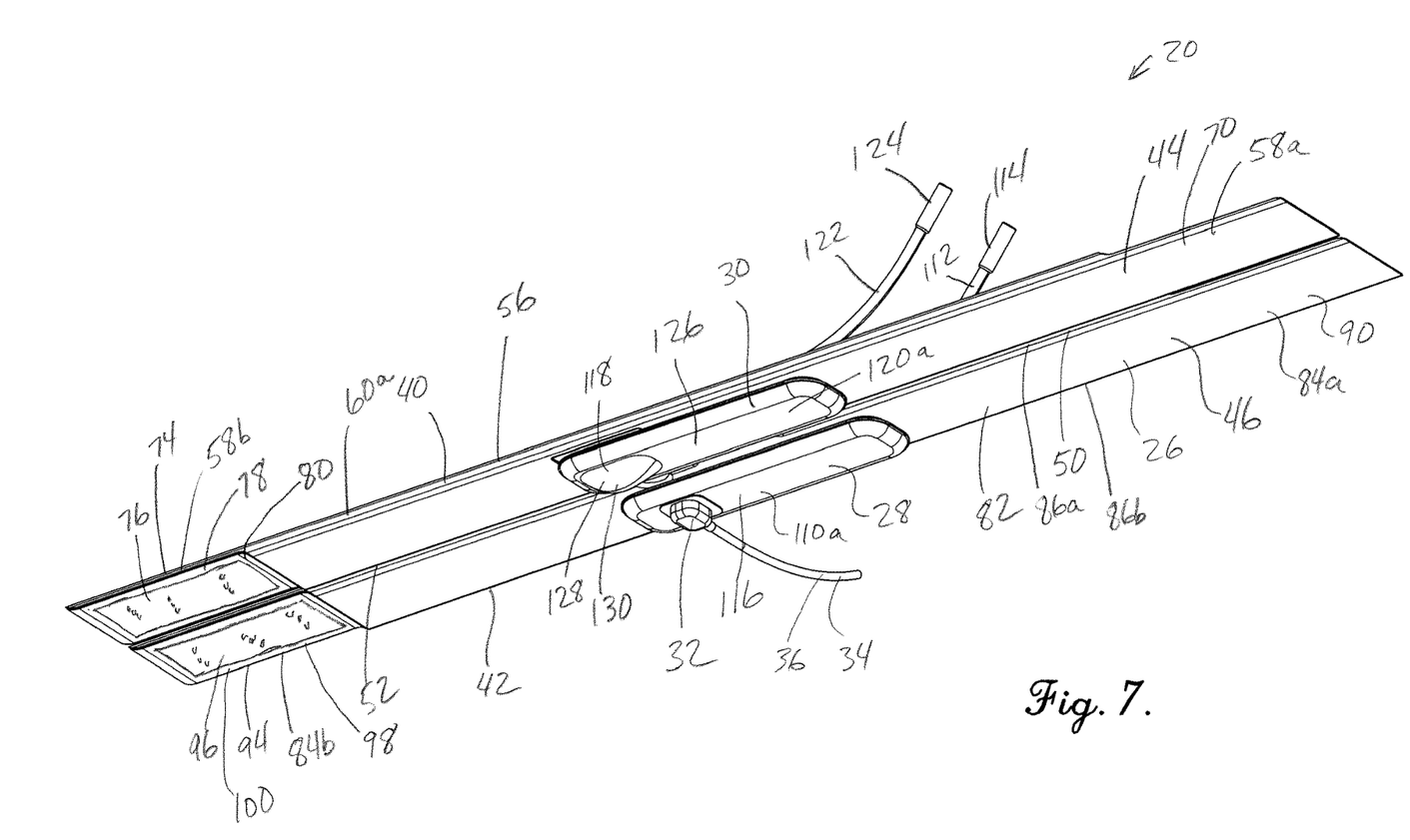
FIG. 7 is a lower perspective of the radial compression band shown in FIGS. 1-6, showing the bladders positioned adjacent to each other.
Figure 8:
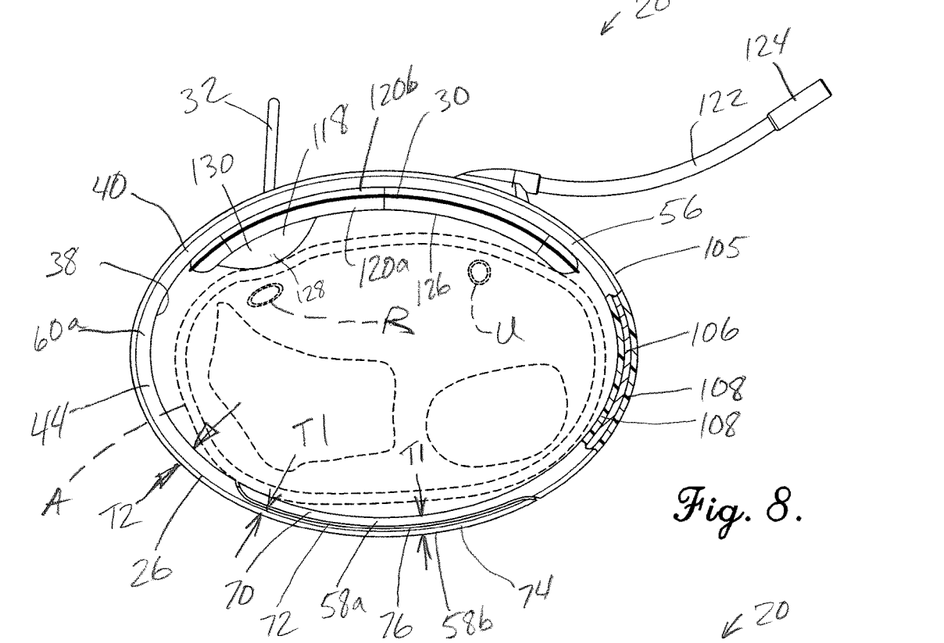
FIG. 8 is a side elevation of the radial compression band shown in FIGS. 1-7, showing the compression band donned by the patient, with the hemostasis bladder being expanded so that the hemostasis pad applies hemostatic pressure to the access site, and with part of the arm band being broken away to show an interior spring band surrounded by a flexible band layer.
Figure 9:
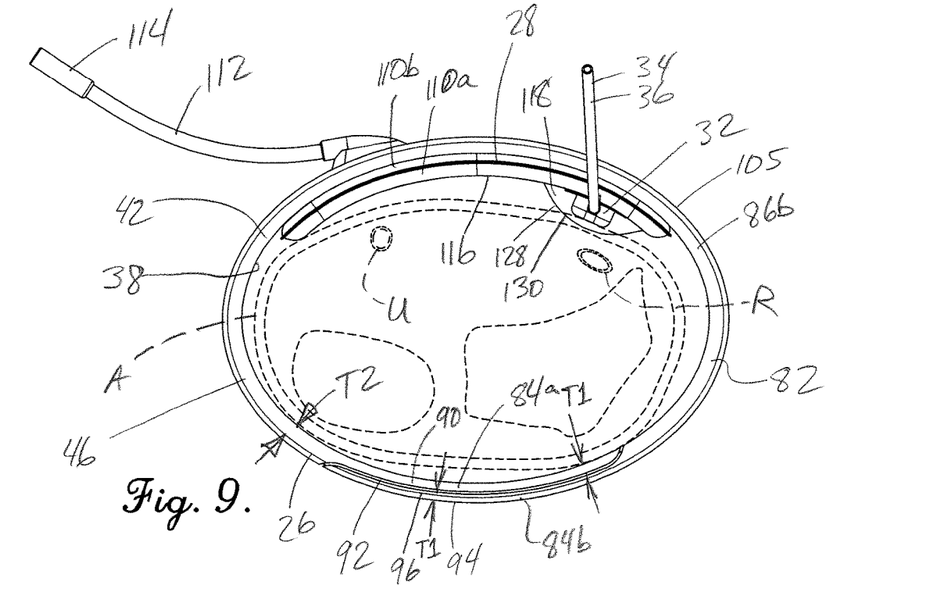
FIG. 9 is a side elevation of the radial compression band viewed in an opposite direction from FIG. 8, showing the probe bladder expanded so that the Doppler probe is held in engagement with the forearm.

Turning to FIGS. 5 and 7, the Doppler probe 32 is preferably coupled to the arm band 26 to sense blood flow through the radial artery R and to thereby facilitate arterial patency during hemostasis of the access site 22.

The Doppler probe 32 includes a transducer and is provided as part of a Doppler ultrasound system 34. The Doppler ultrasound system 34 preferably comprises a dual Doppler instrument that uses Doppler ultrasound to sense vascular blood flow in each of opposite flow directions. In the usual manner, the Doppler ultrasound system 34 preferably includes the Doppler probe 30 and a Doppler unit (not shown) connected to the probe 30 by a cord 36. The Doppler probe 32 is operable to be located adjacent an artery, such as the radial artery R, to sense blood flow through the artery.

The illustrated Doppler probe 32 is preferably attached to the arm band 26, as will be discussed.

When the Doppler probe 32 is positioned with the band 20 on the arm A, the Doppler probe 32 is configured to sense antegrade blood flow and retrograde blood flow through the zone Z of radial artery R.

Turning to FIGS. 4-9, the elongated arm band 26 preferably provides an elongated strength member that can be maintained under tension while applying compression to the access site 22. At the same time, the elongated arm band 26 supports the bladders 28,30 and the Doppler probe 32.

In the illustrated embodiment, the arm band 26 presents an arm opening 38 that extends axially between proximal and distal margins 40,42 to receive the arm A.

The illustrated arm band 26 is preferably sectioned along part of the band length so that the arm band 26 includes proximal and distal arm band sections 44,46. The arm band 26 also includes a connector 48 that joins the band sections to one another 44,46. As will be described, the connector 48 is an integrally formed part of the band 26, although certain aspects of the present invention contemplate use of a separate connector joining the band sections 44,46. It is most preferable, however, that the connector 48 join or interconnect the band sections 44,46 in a manner that allows independent compression for each section, as will also be described.

The band sections 44,46 cooperatively form slots 50,52 that extend along the length of the arm band 26. As will be discussed further, the arm band construction preferably permits the band sections 44,46 to be adjusted independently of one another. Furthermore, the illustrated arm band 26 preferably permits each of the band sections 44,46 to apply pressure to the arm A independently of the other band section 44,46.

The band sections 44,46 also cooperatively present an access opening 54. As will be described, the access opening 54 is configured to receive the catheter sheath 24 when the arm band 26 is donned.

Figure 6:
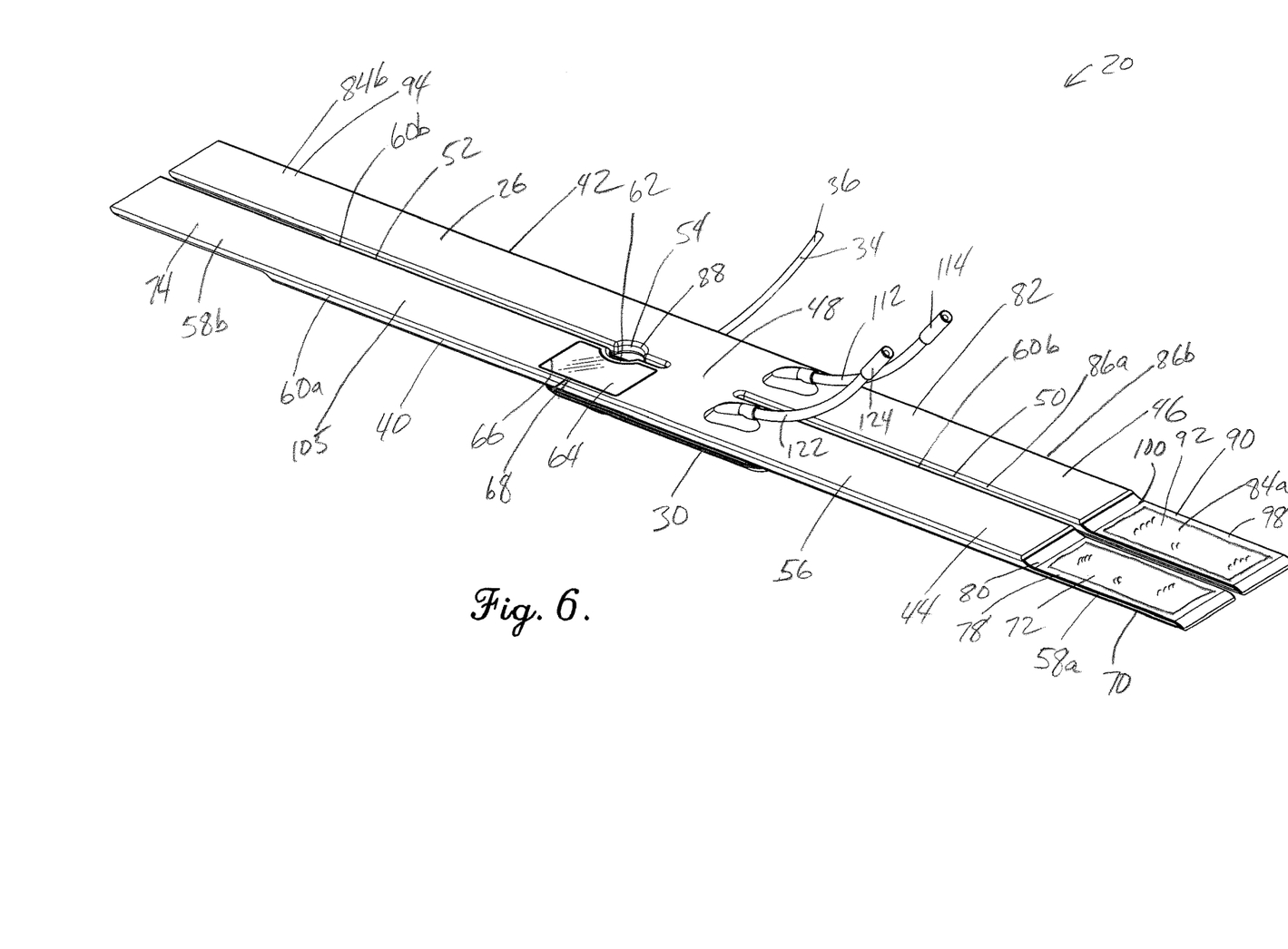
FIG. 6 is an upper perspective of the radial compression band shown in FIGS. 1-5, showing the radial compression band being in an uncoiled configuration.

Preferably, the arm band 26 is shiftable between a coiled configuration (see FIGS. 4 and 5) and a generally flat uncoiled configuration (see FIGS. 6 and 7). In the coiled configuration, the arm band 26 presents a curved shape. Also in the coiled configuration, the end portions preferably overlap one another, although the end portions may not be overlapped for some alternative embodiments. In the uncoiled configuration, the arm band 26 is unwound so that the end portions are spaced from each other.

The proximal band section 44 preferably has a flexible construction and includes an elongated proximal strap portion 56 and inside and outside proximal end portions 58a,b located at opposite ends of the strap portion 56. The strap portion 56 of the proximal arm band section 44 is connected to the distal arm band section 46 by the connector 48.

Figure 10:
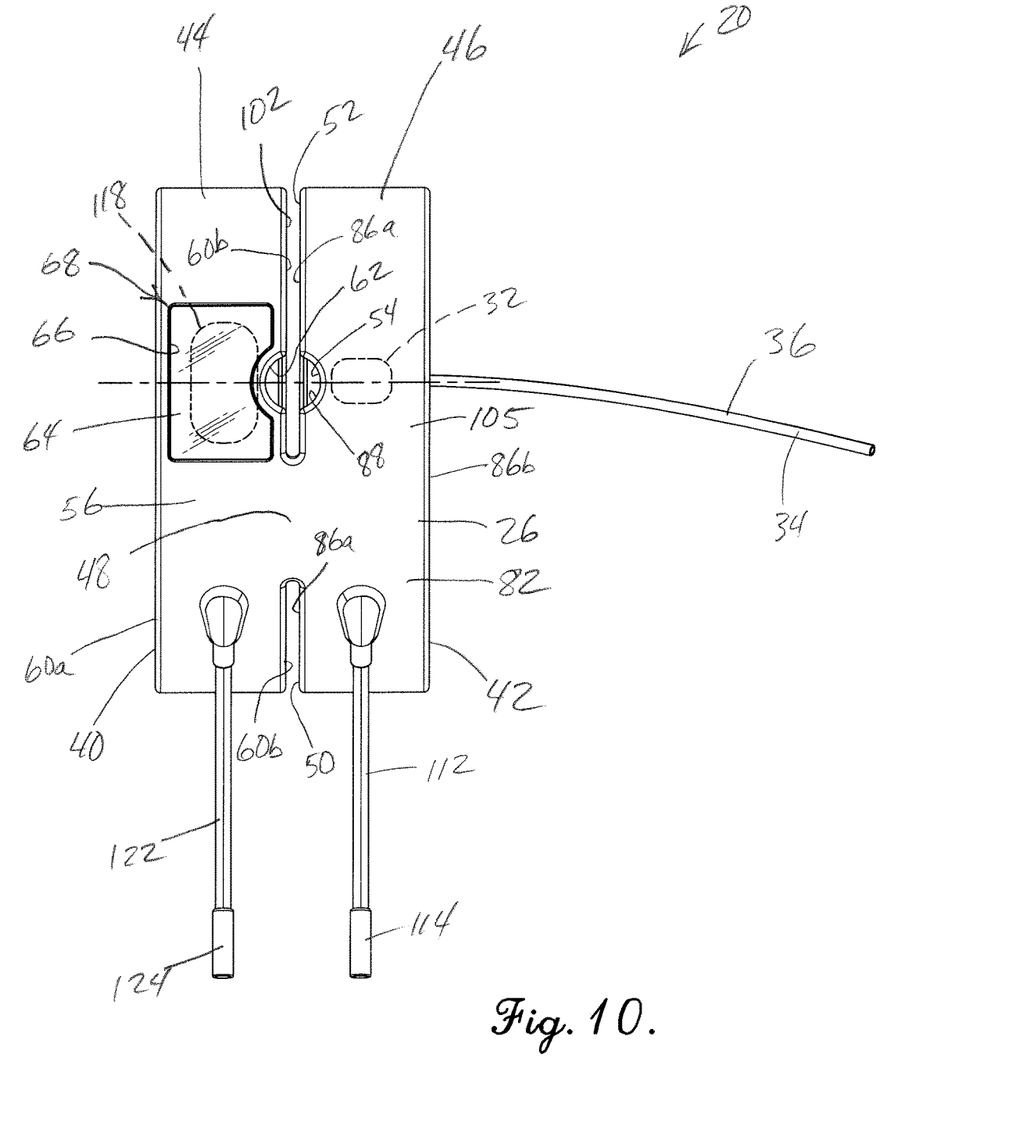
FIG. 10 is a top view of the radial compression band shown in FIGS. 1-9, showing the window, hemostasis pad, Doppler probe, and an access opening of the arm band being circumferentially aligned with each other.

The illustrated proximal arm band section 44 presents proximal and distal edges 60a,b (see FIG. 10) that extend along the length of the proximal arm band section 44. The distal edge 60b defines part of slots 50,52. The distal edge 60b also presents a notch 62 (see FIG. 10) that defines part of the access opening 54.

The proximal arm band section 44 also preferably includes a transparent window section 64 (see FIG. 10) mounted in the strap portion 56. The window section 64 preferably comprises an at least substantially transparent material layer.

As used herein, the term "at least substantially transparent" refers to a material layer that permits underlying objects and anatomy to be seen generally clearly through the material. The material may block or absorb certain wavelengths of light but without appreciable scattering. Because the compression band 20 is flexible, limited scattering might occur when the band is donned, but the intent is for the underlying arm (particularly at or around the access site 22) is visible to the extent necessary to ensure proper positioning of the band and closure of the site. Therefore, the terminology "at least substantially transparent" does not encompass opaque materials. Furthermore, the material should not only be translucent (light transmission is an important component of a transparent material) but also have limited scattering. Most preferably, the term refers to a material layer with a total transmittance of at least about seventy-five percent (75%). As used herein, the term "total transmittance" is the ratio of the amount of light transmitted through the material layer to the amount of light incident on the layer.

In the illustrated embodiment, the strap portion 56 presents a strap opening 66 (see FIG. 10) that receives the window section 64. The illustrated window section 64 is mounted within and spans the strap opening 66 so that the window section 64 defines a window 68. As will be discussed, the window 68 is configured to expose an underlying portion of the arm A, such as the access site 22.

As will be discussed, the arm band 26 includes an interior band and an outer band layer. The illustrated window section 64 is distinct from the interior band and the outer band layer. However, the window section 64 could be formed as an integral part of the outer band layer (e.g., where the window section 64 and the outer band layer are integrally molded onto the interior band).

It will be appreciated that the window 68 could be alternatively shaped and/or positioned on the proximal arm band section 44 to permit viewing of the underlying portion of arm A. While the window 68 is located on the proximal arm band section 44, the arm band 26 could also be configured so that the window 68 is located on the distal arm band section 46. Furthermore, both band sections 44,46 could include one or more windows (e.g., for suitably viewing the arm A). It is also within the ambit of the present invention to position the window 68 against an edge 60a or 60b of the proximal band section 44, such that the window projects from the edge.

Although the window section 64 defines the window 68, the window 68 could be alternatively provided without departing from the scope of the present invention. For instance, the strap opening 66 of the arm band 26 could be devoid of the window section 64, so that the strap opening 66 defines the window itself. That is to say, according to some aspects of the present invention, the window may alternatively be a hole in the corresponding band section. The principles of the present invention also encompass alternative window shapes and materials.

Turning to FIGS. 4-7, the illustrated end portions 58a,b are configured to removably engage each other to secure the proximal arm band section 44 in the coiled configuration. The inside end portion 58a includes a strap element 70 and a hook material strip 72. The outside end portion 58b includes a strap element 74 and a loop material strip 76.

Each strap element 70,74 defines a face 78 (see FIGS. 6 and 7) to receive the respective material strips 72,76. Each strap element 70,74 also presents a thickness dimension T1 that is preferably less than a thickness dimension T2 of the strap portion (see FIG. 8). In this manner, each end portion 58 presents a recess 80 (see FIGS. 6 and 7) to receive the other end portion 58.

The strips 72,76 are adhered to the faces 78 of the corresponding strap elements 70,74 so that the hook material strip 72 and the loop material strip 76 face away from the strap elements 70,74. In the coiled configuration, the material strips 72,76 engage one another to restrict separation of the end portions 58.

However, the hook and loop material strips 72,76 could be attached to opposite ones of the strap elements 70,74. In either configuration, the material strips 72,76 preferably cooperatively provide complemental strips of hook-and-loop fastener material to removably secure the end portions 58 to one another.

As will be appreciated, the material strips 72,76 can be located in various engagement positions with one another. In this manner, the material strips 72,76 enable the end portions 58a,b to be adjustably interconnectible when the arm band 26 is in the coiled configuration.

While the end portions 58 are preferred for removably securing the proximal arm band section 44 in the coiled configuration, the proximal arm band section 44 could be alternatively configured.

In some embodiments, the end portions 58 could be alternatively sized and/or shaped for overlapping engagement. For instance, the end portions 58 could have an alternative strap engagement mechanism, such as a conventional watch band buckle and strap system. However, in other embodiments, the end portions 58 could be configured to secure the arm band 26 on the arm A without overlapping one another.

As will be discussed, the proximal arm band section 44 is preferably donned by initially putting the proximal arm band section 44 in the uncoiled configuration. With the arm band 26 located adjacent to the arm A, the proximal arm band section 44 can be shifted from the uncoiled configuration to the coiled configuration, with the end portions 58 in overlapping engagement with one another. Similarly, the proximal arm band section 44 is preferably removed by shifting the proximal arm band section 44 from the coiled configuration to the uncoiled configuration. Of course, and as will be described, the proximal and distal band sections 44,46 are simultaneously shifted between the coiled and uncoiled configurations.

Turning again to FIGS. 4-9, the distal arm band section 46 also preferably has a flexible construction and includes an elongated distal strap portion 82 and inside and outside distal end portions 84a,b located at opposite ends of the strap portion 82. The strap portion 82 of the distal arm band section 46 is connected to the proximal arm band section 44 by the connector 48.

The illustrated distal arm band section 46 presents proximal and distal edges 86a,b that extend along the length of the band section 46. The proximal edge 86a defines part of the slots 50,52. The proximal edge 86a also presents a notch 88 that defines part of the access opening 54.

Turning again to FIGS. 4-7, the illustrated end portions 84a,b are configured to removably engage each other to secure the proximal arm band section 44 in the coiled configuration. The inside end portion 84a includes a strap element 90 and a hook material strip 92. The outside end portion 84b includes a strap element 94 and a loop material strip 96.

Each strap element 90 defines a face 98 (see FIGS. 6 and 7) to receive the material strips 92,96. Each strap element 90,94 also presents a thickness dimension T1 that is preferably less than a thickness dimension T2 of the strap portion 82 (see FIG. 9). In this manner, each end portion 84 presents a recess 100 (see FIGS. 6 and 7) to receive the other end portion 84.

The strips 92,96 are adhered to the faces 98 of the respective strap elements 90,94 so that the hook material strip 92 and the loop material strip 96 face away from the strap elements 90,94. In the coiled configuration, the material strips 92,96 engage one another to restrict separation of the end portions 84.

However, the hook and loop material strips 92,96 could be attached to opposite ones of the strap elements 90,94. In either configuration, the material strips 92,96 preferably cooperatively provide complemental strips of hook-and-loop fastener material to removably secure the end portions 84 to one another.

As will be appreciated, the material strips 92,96 can be located in various engagement positions with one another. In this manner, the material strips 92,96 enable the end portions 84a,b to be adjustably interconnectible when the arm band 26 is in the coiled configuration.

While the end portions 84a,b are preferred for removably securing the distal arm band section 46 in the coiled configuration, the distal arm band section 46 could be alternatively configured. In some embodiments, the end portions 84a,b could be alternatively sized and/or shaped for overlapping engagement. For instance, the end portions 84a,b could have an alternative strap engagement mechanism, such as a conventional watch band buckle and strap system. However, in other embodiments, the end portions 84a,b could be configured to secure the arm band 26 on the arm A without overlapping one another.

As will be discussed, the distal arm band section 46 is preferably donned by initially putting the distal arm band section 46 in the uncoiled configuration. With the arm band 26 located adjacent to the arm A, the distal arm band section 46 can be shifted from the uncoiled configuration to the coiled configuration, with the end portions 84a,b in overlapping engagement with one another. Similarly, the distal arm band section 46 is preferably removed by shifting the distal arm band section from the coiled configuration to the uncoiled configuration.

The distal edge 60b and proximal edge 86a of the illustrated arm band 26 extend along the length of the corresponding band sections 44,46 and cooperatively define the slots 50,52 and the access opening 54.

Figure 11:
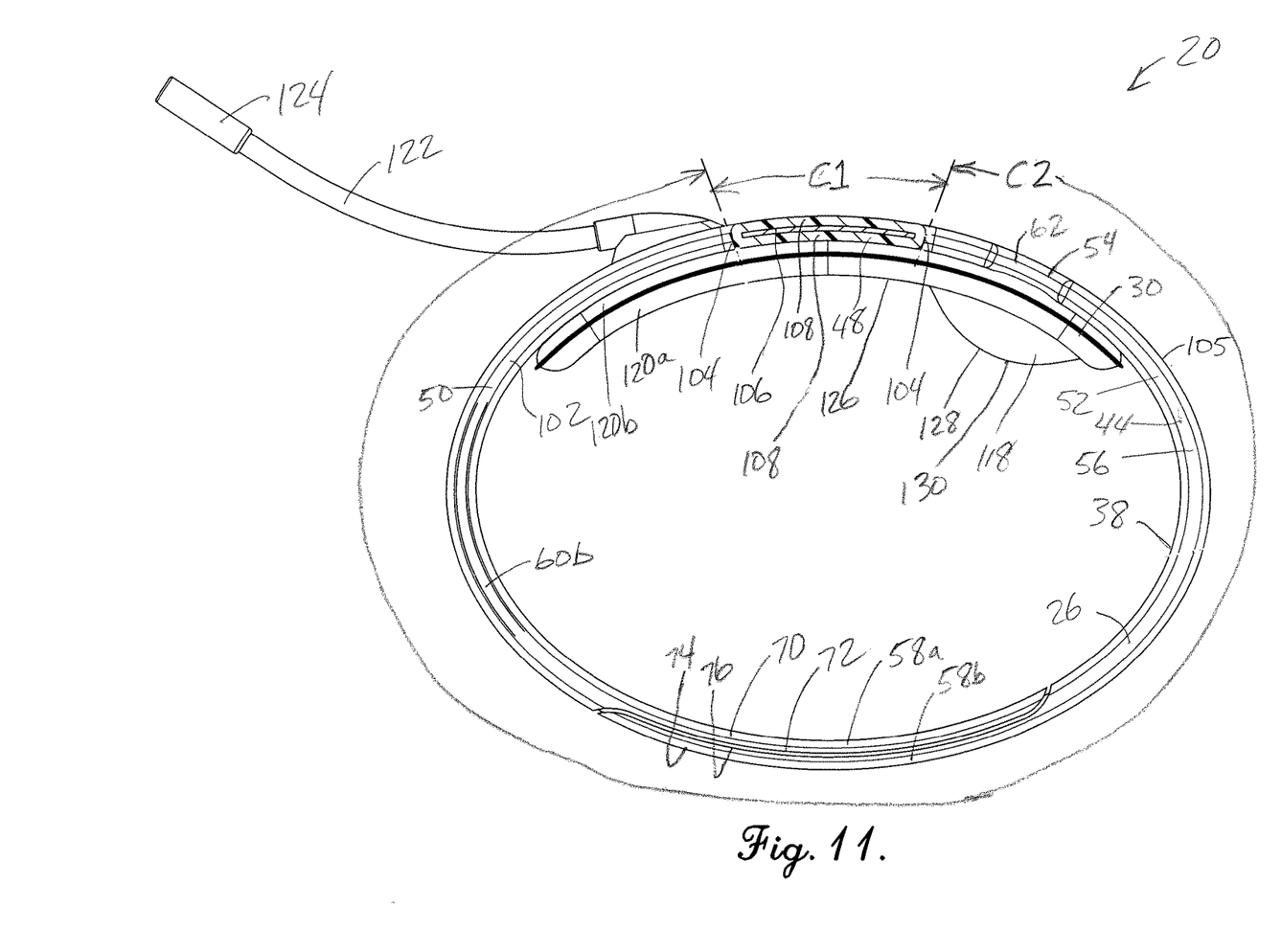
FIG. 11 is a circumferential cross section of the radial compression band shown in FIGS. 1-10, showing the extent of the circumferential slot separating the proximal and distal arm band sections of the arm band.

In the coiled configuration, the slots 50,52 are joined to form a continuous circumferential slot 102 that presents spaced apart slot ends 104 (see FIG. 11). When the arm band 26 is coiled, the arm band 26 presents a total outer circumference dimension measured along an outer surface 105 of the arm band 26. The connector 48 extends between the slot ends 104 to present a connector dimension C1 measured along the outer surface 105 (see FIG. 11). Thus, the slot 102 presents a slot circumference dimension C2 measured along the outer surface 105 (see FIG. 11). The dimension C2 equals the total circumference dimension minus the connector dimension C1.

In the illustrated embodiment, the circumferential slot 102 extends along at least half of the circumferential length of the arm band 26. That is, the slot circumference dimension C2 is at least half of the total circumference dimension. As a result, the arm band sections 44,46 are joined along a circumferential minority of the arm band 26.

More preferably, the slot 102 extends along at least about eighty percent (80%) of the circumferential band length (i.e., the total circumference dimension). However, it is within the scope of the present invention where the slot 102 presents an alternative circumferential length. It will be appreciated that the slot length is selected to permit independent compressive pressure associated with each of the band sections 44,46.

Again, the access opening 54 is configured to receive the catheter sheath 24 when the arm band 26 is donned. The access opening 54 is formed by notches 62,88 presented by the distal edge 60b and proximal edge 86a. The illustrated access opening 54 is defined along the slot 102 and preferably presents a generally circular shape. However, it is within the scope of the present invention where the access opening is alternatively shaped and/or positioned. Furthermore, for some aspects of the present invention, the arm band 26 could be devoid of an access opening to receive the catheter sheath 24 (e.g., where the sheath 24 passes under the distal margin 42).

Again, the connector 48 preferably joins the band sections 44,46 to one another and is an integrally formed part of the band 26. However, it is within the scope of the present invention where the band sections 44,46 are joined or interconnected by a separate connector element. Any alternative connector structure preferably joins or interconnects the band sections 44,46 in a manner that allows independent compression for each section, as will also be described.

Turning again to FIGS. 4-9, the illustrated arm band 26 preferably includes a bistable band structure with an interior spring band 106 and an outer band layer 108 that covers the band 106 (see FIGS. 8 and 11). In particular, the arm band 26 has a bistable band structure that causes the arm band 26 to assume one of two distinct configurations where the shape of the arm band 26 is stable. That is, for each stable configuration, a force must be applied to the arm band 26 to shift the arm band 26 out of the configuration. The stable band configurations include the coiled configuration and the uncoiled configuration.

Again, in the coiled configuration, the arm band 26 preferably presents a curved shape where the corresponding pairs of end portions 58,84 overlap one another. In the uncoiled configuration, the arm band 26 is unwound so that the end portions 58,84 are spaced from each other. Preferably, the arm band 26 assumes a tensioned, relatively straight shape in the uncoiled configuration, although the arm band 26, or a part thereof, could present some curvature.

The interior band 106 preferably includes a strap material that provides the bistable band operation. In particular, the interior strap band preferably comprises a flexible spring band that includes a metallic spring material, although other materials could be used.

The exterior band layer 108 preferably includes a flexible material and, more preferably, includes a synthetic resin material. However, other flexible materials could be used without departing from the scope of the present invention. While the exterior band layer 108 is opaque, the band layer 108 could be at least substantially transparent or at least substantially translucent.

Again, the exterior band layer 108 is preferably distinct from the illustrated window section 64. However, the band layer 108 and the window section 64 could be integrally formed (e.g., where the window section 64 and the band layer 108 are sequentially molded as an integral structure).

Although the arm band 26 preferably has the disclosed bistable structure, for some aspects of the present invention the arm band 26 could be alternatively constructed. For instance, the arm band 26 could be alternatively constructed so that the arm band 26 has a different shape in the coiled configuration and/or the uncoiled configuration.

Also, for some aspects of the present invention, the arm band 26 could have a flexible band structure without having a bistable configuration. For instance, in an alternative construction, the arm band 26 could be removably secured to the arm A with only the hook material strips 72,92 and the loop material strips 76,96. In such an alternative construction, the arm band 26 could be devoid of the interior band 106.

The arm band 26 is preferably donned by initially putting the proximal and distal band sections 44,46 in the uncoiled configuration. With the arm band 26 located adjacent to the arm A, the band sections 44,46 can be shifted from the uncoiled configuration (see FIGS. 6 and 7) to the coiled configuration (see FIGS. 8 and 9), with the corresponding pairs of end portions 58,84 in overlapping engagement with one another. Because the arm band 26 preferably has a bistable configuration, the pairs of end portions 58,84 are snapped into engagement in the coiled configuration.

The sheath 24 is preferably removed from the access site 22 once the band 20 is positioned on the arm A (although the sheath 24 could be removed from the access site 22 before the band is located on the arm A. When donning the arm band 26 while the sheath 24 is inserted in the access site 22, the arm band 26 is configured to slidably receive the sheath 24. In particular, the sheath 24 is passed through the slot 52 and positioned to extend through the access opening 54. While the arm band 26 is donned, the access opening 54 receives the sheath 24 and permits the sheath 24 to extend out of the access opening.

Similarly, the arm band 26 is preferably removed by shifting the band sections 44,46 from the coiled configuration to the uncoiled configuration. Because the arm band 26 preferably has a bistable configuration, the pairs of end portions 58,84 are snapped out of engagement with each other and into the uncoiled configuration.

Turning to FIGS. 7-9 and 11, the hemostasis bladder 30 is selectively expandable and is operable to apply adjustable hemostatic pressure to the access site 22. Similarly, the probe bladder 28 is selectively expandable and is operable to apply adjustable pressure to the Doppler probe 32. As will be discussed, the bladders 28,30 are expandable independently of one another so that the amount of pressure applied to the access site 22 and the amount of pressure applied to the Doppler probe 32 are independently controllable.

The probe bladder 28 is configured to support the Doppler probe 32 in engagement with the arm A when the radial compression band 20 is donned. The probe bladder 28 includes inner and outer bladder walls 110a,b that enclose a chamber (not shown), a bladder fill tube 112 that fluidly communicates with the chamber, and a valve 114 (see FIG. 9). The inner bladder wall 110a presents a probe engagement surface 116 (see FIG. 7).

The probe bladder 28 is attached to the arm band 26 by inserting the tube 112 through an opening (not shown) in the distal arm band section 46. The outer bladder wall 110a is adhered to an inner surface of the distal arm band section 46 with adhesive (not shown).

The valve 114 is operable to be fluidly connected to a syringe (not shown). The probe bladder 28 is configured to be expanded by adding pressurized fluid from the syringe. Similarly, the probe bladder 28 is configured to be contracted by using the syringe to remove fluid from the probe bladder 28. While the fluid used to expand the probe bladder 28 is preferably air, the fluid could alternatively comprise a liquid.

The illustrated probe bladder 28 is positioned radially inward of the distal arm band section 46. Further, the probe bladder 28 is located oppositely from the distal end portions 84 in the coiled configuration.

The probe bladder 28 is preferably at least substantially transparent. However, for some aspects of the present invention, at least part of the probe bladder 28 could be translucent and/or opaque.

Again, the Doppler probe 32 is preferably coupled to the arm band 26 to sense blood flow through the radial artery R to facilitate arterial patency during hemostasis of the access site 22.

The Doppler probe 32 is preferably coupled to the distal arm band section 46 by adhering the Doppler probe 32 to the engagement surface 116 with adhesive (not shown). In the illustrated embodiment, the cord 36 extends distally from the probe 32.

The Doppler probe 32 is operable to be selectively pressed against the arm A by the probe bladder 28. For instance, the amount of pressure applied to the Doppler probe 32 can be increased by adding pressurized fluid (preferably air) from the syringe to expand the probe bladder 28. Similarly, the amount of pressure applied to the Doppler probe 32 can be reduced by removing pressurized fluid from the probe bladder 28 with the syringe to contract the probe bladder 28.

Preferably, the bladder 28 provides the primary pressure adjustment mechanism to selectively apply pressure to the Doppler probe 32. However, the arm band 26 could include an alternative mechanism to adjustably press the probe 32 against the arm A. For instance, the hook and loop material strips 92,96 of the distal arm band section 46 could be used alternatively to, or in combination with, the bladder 28 to adjustably press the probe 32 against the arm A. Yet further, it will be appreciated that another pressure adjustment device (e.g., an alternative adjustable connection device for the strap ends, an alternative expandable component, etc.) could be used to selectively apply pressure to the Doppler probe 32 without departing from the scope of the present invention.

With the Doppler probe 32 mounted on the distal arm band section 46, the access opening 54 is preferably located axially between the hemostasis bladder 30 and the Doppler probe 32. Furthermore, the access opening 54 is located axially between the window 68 and the Doppler probe 32.

Again, the band 20 is preferably configured to achieve hemostasis of the access site 22 while the Doppler probe 32 senses blood flow through the zone Z of the radial artery R. When the band 20 is donned, the Doppler probe 32 is preferably located along the zone Z and is operable to sense blood flow through the zone Z. This includes sensing whether the blood flow is antegrade flow or retrograde flow.

For instance, the Doppler probe 32 is configured to sense antegrade flow when hemostasis of the access site 22 is achieved along with patency of the radial artery R. Similarly, the Doppler probe 32 is configured to sense retrograde flow in various conditions (e.g., when part of the radial artery R adjacent the access site 22 is collapsed and occluded).

Referring again to FIGS. 7-9 and 11, the hemostasis bladder 30 is configured to support a hemostasis pad 118 in engagement with the arm A when the radial compression band 20 is donned. The hemostasis bladder 30 includes inner and outer bladder walls 120a,b that enclose a chamber (not shown), a bladder fill tube 122 that fluidly communicates with the chamber, and a valve 124 (see FIG. 9). The inner bladder wall 120a presents a pad engagement surface 126 (see FIG. 7).

The hemostasis bladder 30 is attached to the arm band 26 by inserting the tube 122 through an opening (not shown) in the proximal arm band section 44. The outer bladder wall 120b is adhered to an inner surface of the proximal arm band section 44 with adhesive (not shown).

The valve 124 is operable to be fluidly connected to a syringe (not shown). The hemostasis bladder 30 is configured to be expanded by adding pressurized fluid from the syringe. Similarly, the hemostasis bladder 30 is configured to be contracted by using the syringe to remove fluid from the hemostasis bladder 30. While the fluid used to expand the hemostasis bladder 30 is preferably air, the fluid could alternatively comprise a liquid.

Preferably, the illustrated hemostasis bladder 30 is positioned radially inward of the window 68 and spans the window 68. In the illustrated embodiment, the bladder 30 spans the window 68 in both the axial and circumferential directions.

The hemostasis bladder 30 is supported by the proximal arm band section 44 on opposite proximal and distal sides of the window 68. The bladder 30 is also supported by the proximal arm band section 44 on opposite axially extending sides of the window 68. Further, the hemostasis bladder 30 is preferably axially aligned with the window 68.

However, the principles of the present invention are applicable where the hemostasis bladder 30 is alternatively positioned relative to the proximal arm band section 44. For instance, the hemostasis bladder 30 could be positioned to extend across only part of the window 68 (e.g., where the hemostasis bladder 30 does not span the window 68 in any direction). In a similar alternative configuration, the hemostasis bladder 30 may not be supported by the proximal arm band section 44 on opposite sides of the window 68.

The hemostasis bladder 30 is preferably at least substantially transparent so as to facilitate viewing of the access site 22. However, for some aspects of the present invention, at least part of the hemostasis bladder 30 could be translucent and/or opaque.

As used herein, the term "viewing of the access site 22" refers to viewing of the catheter opening in the arm A and the area adjacent to the catheter opening. In at least some embodiments, this area is the area located within about one centimeter (1 cm) of the catheter opening.

The pad 118 preferably presents an arterial pressure surface 128 that faces radially inwardly relative to the arm band 26 for compressive engagement with the access site 22. The pad 118 preferably includes a flexible body 130 that presents the pressure surface 128 and an internal pocket (not shown). The pad 118 also preferably includes a gel material that fills the pocket. The deformable gel-filled construction of the pad 118 is operable to deform in response to compressive engagement with the access site 22.

The illustrated pressure surface has an elongated convex form that presents a generally ellipsoidal shape. However, the pressure surface could have an alternative shape without departing from the scope of the present invention.

In the most preferred embodiment, the pad 118 and at least the pressure surface 128 are at least substantially transparent. However, in some embodiments, the body 130 and the gel material of the pad are substantially translucent, which still provides some visibility of the access site 22. As used herein, the term "substantially translucent" refers to a material layer that is not opaque. Furthermore, the term refers to a material layer with a total transmittance of at least about fifty percent (50%). However, for some aspects of the present invention, at least part of the pad 118 could be opaque.

The pad 118 is preferably coupled to the proximal arm band section 44 by adhering the pad 118 to the pad engagement surface 126. Thus, the pad 118 projects radially inwardly from the inner bladder wall 120*a* to present the pressure surface 128.

However, the principles of the present invention are applicable where the pad 118 is alternatively fixed to the hemostasis bladder 30. For instance, the pad 118 could be integrally formed with the hemostasis bladder 30.

Alternatively, the pad 118 could be provided with but detached from the bladder 30. In such an alternative embodiment, the pad 118 could be adhered to the access site 22 prior to donning the band 20. With the pad 118 attached directly to the access site 22, the band 20 can be donned so that the bladder 30 engages the pad 118.

Yet further, for some aspects of the present invention, an alternative hemostasis band could be constructed so that the band is devoid of the pad 118. For instance, an alternative hemostasis band could have a hemostasis bladder with a bladder wall that engages the access site directly, with hemostatic pressure being applied directly by the bladder wall.

Again, with the Doppler probe 32 mounted on the distal arm band section 46, the access opening 54 is located between the hemostasis bladder 30 and the Doppler probe 32. With the Doppler probe 32 mounted on the distal arm band section 46, the pressure surface 128 and Doppler probe 32 are spaced axially on the arm band 26, and the Doppler probe 32 is located distally of the pressure surface 128. More particularly, the access opening 54 is located axially between the pressure surface 128 and the Doppler probe 32.

In the illustrated embodiment, the pressure surface 128, Doppler probe 32, and access opening 54 are most preferably aligned circumferentially along the arm band 26. Also, the access opening 54 is most preferably spaced at least substantially equidistant between the pressure surface 128 and the Doppler probe 32. However, for some aspects of the present invention, the relative positioning of the pressure surface 128, Doppler probe 32, and access opening 54 could be altered.

As described previously, the arm band 26 includes band sections 44,46 and a connector 48 that preferably joins the band sections 44,46 to one another. However, according to some aspects of the present invention, the band sections 44,46 could be unjoined, such that the arm band 26 is formed of multiple (preferably two (2)) separate, detached, spaced apart band sections. (Such an alternative arm band consists of at least two (2) unjoined bands that still cooperatively prevent the proximal and distal margins of the overall band and the arm opening extending between the margins.) For example, with regard to the preferred circumferential alignment of the pressure surface 128, Doppler probe 32, and access opening 54, it is within the ambit of the present invention to form the arm band 26 of unjoined band sections while maintaining the preferred circumferential alignment of these components. In other words, the band 20 could be used with detached band sections where circumferential alignment of the pressure surface, Doppler probe, and access opening is generally maintained. In such an alternative embodiment, the access opening could be formed by merely spacing the detached band sections apart from each other.

Similarly, certain aspects of the present invention encompass an arm band that is not sectioned. That is to say, it is within the ambit of the present invention to use a single, unitary band devoid of a circumferential slot in connection with some of the novel aspects described herein. For example, the pressure surface 128, Doppler probe 32, and access opening 54 may be provided in circumferential alignment on a non-sectioned band. Again, as long as circumferential alignment of the pressure surface 128, Doppler probe 32, and access opening 54 is maintained, certain aspects of the present invention permit the use of a non-sectioned band.

The pad 118 is operable to be selectively pressed against the access site 22 to achieve hemostasis of the access site 22 while maintaining arterial patency. In the illustrated embodiment, the pad 118 is operable to be pressed against the access site 22 by the hemostasis bladder 30. The amount of pressure applied to the pad 118 can be increased by adding pressurized fluid (preferably air) from the syringe to expand the hemostasis bladder 30. Similarly, the amount of pressure applied to the pad 118 can be reduced by removing pressurized fluid from the hemostasis bladder 30 with the syringe to contract the hemostasis bladder 30.

Preferably, the hemostasis bladder 30 provides the primary pressure adjustment mechanism to selectively apply pressure to the pad 118. However, the arm band 26 could include an alternative mechanism to position the pad 118 and to adjustably press the pad 118 against the arm A. For instance, the hook and loop material strips 72,76 of the proximal arm band section 44 could be used alternatively to, or in combination with, the bladder 30 to adjustably press the pad 118 against the arm A. Yet further, it will be appreciated that another pressure adjustment device (e.g., an alternative adjustable connection device for the strap ends, an alternative expandable component, etc.) could be used to selectively apply pressure to the pad 118 without departing from the scope of the present invention.

Again, the band 20 is preferably configured to achieve hemostasis of the access site 22 while the Doppler probe 32 senses blood flow through the zone Z of the radial artery R. When the band 20 is donned, the pad 118 is located in compressive engagement with the access site. At the same time, the band 20 is also preferably positioned so that the Doppler probe 32 is located along the zone Z and is operable to sense blood flow through the zone Z. This includes sensing whether the blood flow is antegrade flow or retrograde flow.

Again, the Doppler probe 32 is configured to sense antegrade flow when hemostasis of the access site 22 is achieved along with patency of the radial artery R. Similarly, the Doppler probe 32 is configured to sense retrograde flow in various conditions (e.g., when part of the radial artery R adjacent the access site 22 is collapsed and occluded).

The bladders 28,30 are preferably configured so that the amount of fluid in each bladder 28,30 can be adjusted independently of the amount of fluid in the other bladder. In this manner, the amount of engagement pressure applied to the Doppler probe 32 by the probe bladder 28 can be adjusted independently of the amount of engagement pressure applied to the pad 118 by the hemostasis bladder 30.

In use, the radial compression band 20 provides hemostatic compression to an arterial access site 22 on the arm A of a wearer while maintaining patency of the radial artery R.

With the sheath 24 inserted in the access site 22, the band 20 is donned by initially putting the band 20 in the uncoiled configuration. With the arm band 26 located adjacent to the arm A, the band 20 can be shifted from the uncoiled configuration to the coiled configuration, with the corresponding pairs of end portions 58,84 in overlapping engagement with one another. Because the arm band 26 preferably has a bistable configuration, the pairs of end portions 58,84 are snapped into engagement in the coiled configuration. The end portions 58,84 are also secured to one another by hook-and-loop fastener engagement, as discussed above.

The sheath 24 can be removed from the access site 22 either before or after the band 20 is positioned on the arm A. When donning the arm band 26 while the sheath 24 is inserted in the access site 22, the arm band 26 is configured to slidably receive the sheath 24. In particular, the sheath 24 is passed through the slot 52 and positioned to extend through the access opening 54. With the arm band 26 being donned, the access opening 54 receives the sheath 24 and permits the sheath 24 to extend out of the access opening 54.

The band 20 is preferably configured to achieve hemostasis of the access site 22 while the Doppler probe 32 senses blood flow through the zone Z of the radial artery R. When the band 20 is donned, the pad 118 is located in compressive engagement with the access site 22. At the same time, the band 20 is also preferably positioned so that the Doppler probe 32 is located along the zone Z and is operable to sense blood flow through the zone Z. This includes sensing whether the blood flow is antegrade flow or retrograde flow.

Once hemostasis of the access site 22 is achieved, the arm band 26 is preferably removed by shifting the band sections 44,46 from the coiled configuration to the uncoiled configuration. Because the arm band 26 preferably has a bistable configuration, the pairs of end portions 58,84 are snapped out of engagement with each other and into the uncoiled configuration.

The preferred forms of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventor hereby states his intent to rely on the Doctrine of Equivalents to determine and assess the reasonably fair scope of the present invention as pertains to any apparatus not materially departing from but outside the literal scope of the invention as set forth in the following claims.

What is claimed is:

1. A radial compression band configured to provide hemostatic compression to an arterial access site on the arm of a wearer after an arterial sheath is removed from the access site, said radial compression band comprising:
    an elongated arm band presenting an inner surface, an outer surface, and an arm opening defined at least partly by the inner surface and sized to receive the arm,
    said arm band presenting proximal and distal margins, with the arm opening being defined between the margins;
    an arterial pressure surface facing radially inward relative to the arm band for compressive engagement with the access site; and
    a Doppler probe coupled to the arm band and spaced from the pressure surface to sense blood flow through the artery and thereby facilitate arterial patency during hemostasis of the access site, with spacing between the pressure surface and Doppler probe providing an open area configured to overlie the access site,
    said arm band presenting an access opening located between the pressure surface and the Doppler probe,
    said access opening extending continuously through the arm band from the outer surface to intersect the inner surface at a location aligned with the open area between the pressure surface and the Doppler probe, with the access opening being configured to receive the arterial sheath and permit the arterial sheath to pass directly through the arm band to the access site when the radial compression band is donned.

2. The radial compression band as claimed in claim 1, said access opening presenting a generally circular shape.

3. The radial compression band as claimed in claim 1, said arm band being partly sectioned to include circumferentially extending, proximal and distal arm band sections, with the access opening being located between the arm band sections.

4. The radial compression band as claimed in claim 3, said arm band presenting a circumferential slot defined between the band sections, said slot defining the access opening.

5. The radial compression band as claimed in claim 4, said slot extending along at least half of the circumferential length of the arm band, such that the arm band sections are joined along a circumferential minority of the arm band.

6. The radial compression band as claimed in claim 1, said arm band presenting a window located at least in part between the proximal and distal margins so as to expose the underlying portion of the arm,
    said pressure surface being positioned at least in part radially inward of the window,
    said access opening being located between the window and the Doppler probe.

7. The radial compression band as claimed in claim 6, further comprising:
    an expandable bladder presenting the pressure surface.

8. The radial compression band as claimed in claim 7, said bladder including a bladder wall and a hemostasis pad that projects radially inwardly from the bladder wall to present the pressure surface.

9. The radial compression band as claimed in claim 8, said hemostasis pad comprising a deformable gel-filled body.

10. The radial compression band as claimed in claim 7, said bladder spanning the window, with the bladder being supported by the arm band on opposite sides of the window.

11. The radial compression band as claimed in claim 7, further comprising:
    a second expandable bladder coupled to the arm band to extend radially inwardly relative to the arm band,
    said second bladder being configured to support the Doppler probe for adjustably compressible engagement with the arm when the radial compression band is donned.

12. The radial compression band as claimed in claim 11, said arm band being partly sectioned to include circumferentially extending proximal and distal arm band sections,
    each of said bladders being coupled to a corresponding one of the band sections.

13. The radial compression band as claimed in claim 6, said arm band including a window section that defines the window,
    said window section comprising an at least substantially transparent material layer.

14. The radial compression band as claimed in claim 1, said access opening being spaced at least substantially equidistant between the pressure surface and the Doppler probe.

15. The radial compression band as claimed in claim 1, said arm opening extending axially between the proximal and distal margins, said pressure surface and Doppler probe being spaced axially on the arm band, said access opening being located axially between the pressure surface and the Doppler probe.

16. The radial compression band as claimed in claim 15, said pressure surface, Doppler probe, and access opening being aligned circumferentially along the arm band.

17. The radial compression band as claimed in claim 1, said arm band having a bistable construction to assume a coiled configuration or an uncoiled configuration.

18. The radial compression band as claimed in claim 17, said arm band including a flexible spring band presenting a curved shape when the arm band is in the coiled configuration and a tensioned, relatively straight shape when the arm band is in the uncoiled configuration.

19. The radial compression band as claimed in claim 17, said arm band presenting opposite ends that are adjustably interconnectable when the arm band is in the coiled configuration.

20. The radial compression band as claimed in claim 19,
said ends of the arm band overlapping one another when the arm band is in the coiled configuration,
said arm band including complemental strips of hook-and-loop fastener material adjacent the ends to provide adjustable interconnection thereof when the arm band is in the coiled configuration.

21. A radial compression band configured to provide hemostatic compression to an arterial access site on the arm of a wearer after an arterial sheath is removed from the access site, said radial compression band comprising:
an elongated arm band presenting an inner surface, an outer surface, and an arm opening defined at least partly by the inner surface and sized to receive the arm,
said arm band presenting proximal and distal margins, with the arm opening being defined between the margins;
an arterial pressure surface facing radially inward relative to the arm band for compressive engagement with the access site; and
a Doppler probe coupled to the arm band and spaced from the pressure surface to sense blood flow through the artery and thereby facilitate arterial patency during hemostasis of the access site, with spacing between the pressure surface and Doppler probe providing an open area configured to overlie the access site,
said arm band presenting an access opening located between the pressure surface and the Doppler probe,
said access opening extending continuously through the arm band from the outer surface to intersect the inner surface at a location aligned with the open area between the pressure surface and the Doppler probe, with the access opening being configured to receive the arterial sheath and permit the arterial sheath to pass directly through the arm band to the access site when the radial compression band is donned,
said pressure surface, Doppler probe, and access opening being aligned circumferentially along the arm band.

22. The radial compression band as claimed in claim 21,
said arm band presenting a window located at least in part between the proximal and distal margins so as to expose the underlying portion of the arm,
said pressure surface being positioned at least in part radially inward of the window,
said access opening being located between the window and the Doppler probe.

23. The radial compression band as claimed in claim 22, further comprising:
an expandable bladder presenting the pressure surface.

24. The radial compression band as claimed in claim 21,
said arm band being partly sectioned to include circumferentially extending proximal and distal arm band sections.

25. The radial compression band as claimed in claim 24,
said arm band presenting a circumferential slot defined between the sections along at least half of the circumferential length of the arm band, such that the arm band sections are joined along a circumferential minority of the arm band.

26. The radial compression band as claimed in claim 25,
said slot defining the access opening.

27. A radial compression band configured to provide hemostatic compression to an arterial access site on the arm of a wearer after an arterial sheath is removed from the access site, said radial compression band comprising:
an elongated arm band presenting an arm opening sized to receive the arm,
said arm band presenting proximal and distal margins, with the arm opening being defined between the margins;
an arterial pressure surface facing radially inward relative to the arm band for compressive engagement with the access site;
a Doppler probe coupled to the arm band and spaced from the pressure surface to sense blood flow through the artery and thereby facilitate arterial patency during hemostasis of the access site,
said arm band presenting an access opening located between the pressure surface and the Doppler probe, with the access opening being configured to receive the arterial sheath when the radial compression band is donned,
said pressure surface, Doppler probe, and access opening being aligned circumferentially along the arm band,
said arm band presenting a window located at least in part between the proximal and distal margins so as to expose the underlying portion of the arm,
said pressure surface being positioned at least in part radially inward of the window,
said access opening being located between the window and the Doppler probe, further comprising; and
an expandable bladder presenting the pressure surface,
said bladder being positioned at least in part radially inward of the window and extending across at least part of the window,
said bladder being at least substantially transparent so as to facilitate viewing of the access site.

* * * * *